United States Patent
Kawabe et al.

(10) Patent No.: US 6,869,791 B2
(45) Date of Patent: Mar. 22, 2005

(54) METHOD FOR STERILIZING TRANSFORMED CELLS

(75) Inventors: Tomoyasu Kawabe, Nishinomiya (JP); Kae Hiramine, Kobe (JP)

(73) Assignee: Sumitomo Chemical Company, Ltd., Osaka (JP)

( * ) Notice: Subject to any disclaimer, the term of this patent is extended or adjusted under 35 U.S.C. 154(b) by 251 days.

(21) Appl. No.: 09/999,170

(22) Filed: Dec. 3, 2001

(65) Prior Publication Data

US 2003/0044894 A1 Mar. 6, 2003

(30) Foreign Application Priority Data

Dec. 4, 2000 (JP) ........................................ 2000-368180

(51) Int. Cl.$^7$ .............................. C12N 1/32; C12N 1/00
(52) U.S. Cl. ........................................ 435/247; 435/243
(58) Field of Search ............................... 435/243, 247, 435/196

(56) References Cited

U.S. PATENT DOCUMENTS

| | | |
|---|---|---|
| 4,612,169 A | 9/1986 | Iwasaki et al. |
| 4,680,262 A | 7/1987 | Bochner et al. |
| 4,966,844 A | 10/1990 | Tallen et al. |
| 5,137,821 A | 8/1992 | Sagai et al. |

FOREIGN PATENT DOCUMENTS

| | | |
|---|---|---|
| EP | 0 497 103 A2 | 8/1992 |
| EP | 0 969 094 A2 | 1/2000 |
| EP | 1 057 894 A2 | 12/2000 |
| JP | 59-55186 A | 3/1984 |
| JP | 06 030774 A | 8/1994 |

OTHER PUBLICATIONS ilngram, L.O., et al. (1980) J. Bacteriol. 144(2), 481–488.*
Bokinbobai No. Kagaku, Published by Sankyo–Shuppan Co. on Jan. 10, 1982.

Nishizawa et al., "Stereoselective Production of (+)-*trans*-Chrysanthemic Acid by a Microbial Esterase: Cloning, Nucleotide Sequence, and Overexpression of the Esterase Gene of *Arthrobacter Globiformis* in *Escherichia Coli*," Applied and Environmental Microbiology, vol. 61, No. 9, pp. 3208–3215 (Sep. 1995).

Toida et al., "Cloning and Sequencing of the Triacylglycerol Lipase Gene of *Aspergillus Oryzae* and Its Expression in *Escherichia Coli*," FEMS Microbiology Letters, 189, pp 159–164 (2000).

Field et al., "Biological Elimination of Polycyclic Aromatic Hydrocarbons in Solvent Extracts of Polluted Soil by the White Rot Fungus, *Bjerkandera* SP, Strain BOS55," Environmental Technology, vol. 17, pp. 317–323 (1996).

Ingram, L.O., "Mechanism of Lysis of *Escherichia Coli* by Ethanol and Other Chaotropic Agents," Journal of Bacteriology, vol. 146, No. 1, pp. 331–336 (Apr. 1981).

Database EMBL oNLINE! EBI; Aug. 23, 2000, Toida J. et al.: "*Aspergillus Oryzae* TgIa Gene For Triacylglycerol Lipase, Complete CDs"; Database Accession No. AB039325, XP002229311.

Anonymous: From Analytical To Preparative/Industrial Mitsubishi Chemical, Online! Dec. 23, 1999, XP002229312, Retrieved from Internet.

* cited by examiner

*Primary Examiner*—Charles L. Patterson, Jr.
(74) *Attorney, Agent, or Firm*—Fitch, Even, Tabin & Flannery

(57) ABSTRACT

There is provided a method for sterilizing a transformed microorganism, which is characterized by mixing at a temperature range of 25° C. or higher to less than 35° C. a solution containing a transformed microorganism belonging to *Escherichia* introduced with a DNA coding for an enzyme having a thermal denaturation temperature of 50° C. or higher, with at least one member selected from the group consisting of monovalent alcohols having one to three carbon atoms and acetone, in an amount of 10 to 35% by weight of the solution.

17 Claims, No Drawings

METHOD FOR STERILIZING TRANSFORMED CELLS

FIELD OF THE INVENTION

The present invention relates to a method for sterilizing transformed microorganisms without inactivating activity of useful enzymes expressed in transformed microorganisms.

BACKGROUND OF THE INVENTION

With recent developments in genetic engineering technologies, enzymes produced by transformed microorganisms are widely used. In view of the environmental safety, it has been required to prevent transformed microorganisms, which do not exist in nature, from being transmitted or diffused in the environment. In order to satisfy such requirements, physical and/or chemical disruption processes for sterilization of microorganisms are employed.

Physical containment of the transformed microorganisms used for producing enzymes requires suitable heavy equipments, particularly for industrial scale of production. Conventional method of sterilizing transformed microorganisms has a disadvantage in that the activity of the enzymes to be recovered is often impaired by inactivation under sterilizing conditions.

SUMMARY OF THE INVENTION

According to the present invention, certain transformed 25 microorganisms are suitably sterilized, thereby desired enzymes produced by the transformed microorganism cells are readily recovered without significant loss of their activity.

The present invention provide a method for sterilizing a transformed microorganism, which comprises mixing at a temperature range of from 25° C. or higher to less than 35° C. a solution containing a transformed microorganism belonging to Escherichia introduced with a DNA coding for an enzyme having a thermal denaturation temperature of 50° C. or higher, with at least one member selected from the group consisting of monovalent alcohols having one to three carbon atoms and acetone, in an amount of 10 to 35% by weight of the solution (hereinafter referred to as "the present method").

DETAILED DESCRIPTION OF THE INVENTION

Microorganisms belonging to Escherichia are suitably used as the host microorganism in the present method. Particularly, microorganisms belonging to Escherichia coli are preferably used in view of good availability in the preparation of transformed microorganisms, and more preferably used is a microorganism of Escherichia coli JM 105 strain.

The DNA coding for an enzyme having a thermal denaturation temperature of 50° C. or higher is introduced into the Escherichia microorganisms to transform the same. The thermal denaturation temperature of an enzyme herein means a temperature at which the changing ratio in the measured value of a circular dichroism spectrum of the enzyme is the greatest. For example, the thermal denaturation temperature can be known by measuring the maximum change ratio in the circular dichroism spectrum of an enzyme solution, which typically contains the enzyme at a concentration of about 1 g/ml to about 50 µg/ml in a 10 mM sodium phosphate buffer solution (pH 6.5 to pH 7.5), at a wavelength of 222 nm with a circular dichroism spectrometer, while the temperature being changed, typically from 40° C. to 70° C., at a ratio such as about 1° C./1 min or less.

Examples of the enzyme having a thermal denaturation temperature of 50' or higher include, for example, an enzyme having a thermal denaturation temperature of 53° C. or higher, and an enzyme having a thermal denaturation temperature of 60° C. or higher. The upper limit of the thermal denaturation temperature is not particularly limited, and is typically 80° C. or less.

Examples thereof include, for example, an oxidoreductase having a thermal denaturation temperature of 50° C. or higher, a transferase having a thermal denaturation temperature of 50° C. or higher, a hydrolase having a thermal denaturation temperature of 50° C. or higher, a lyase having a thermal denaturation temperature of 50° C. or higher, an isomerase having a thermal denaturation temperature of 50° C. or higher and a ligase having a thermal denaturation temperature of 50° C. or higher, and preferred is an esterase originating from Aspergillus, Arthrobacter, or Chromobacterium.

The DNA coding for the amino acid sequence of the enzyme having a thermal denaturation temperature of 50° C. or higher may be a nucleic acid sequence that codes for an amino acid sequence provided with a specific mutation to enhance thermal stability to an enzyme, or a nucleic acid that is not provided with such an artificial mutation.

Examples of the nucleic acid sequence coding for the enzyme having thermal denaturation temperature of 50° C. or higher include, for example, (a) a nucleic acid sequence of SEQ ID NO. 1;
(b) a nucleic acid sequence:
hybridizing under stringent conditions with the nucleic acid sequence of SEQ ID NO. 1, and
coding for an amino acid sequence (SEQ ID NO: 10) of an enzyme capable of asymmetrically hydrolyzing a racemic N-benzylazetidin-2-carboxyilic acid ethyl ester to preferentially produce (S)-N-benzylazetidin-2-carboxylic acid;
(c) a nucleic acid sequence of SEQ ID NO. 2;
(d) a nucleic acid sequence:
hybridizing under stringent conditions with the nucleic acid sequence of SEQ ID NO. 2, and
coding for an amino acid sequence (SEQ ID NO: 11) of an enzyme capable of asymmetrically hydrolyzing a chrysanthemic acid ester derivative, (for example, 2,2-dichloro-3-(1-propenyl) cyclopropane-1-carboxylic acid esters, 2,2-dimethyl-3-(2-chloro-1-propenyl)cyclopropane-1-carboxylic acid esters, 2,2-dimethyl-3-(1-propenyl)cyclopropane-1-carboxylic acid esters, 2,2-dimethyl-3-(2-chloro-2-fluorovinyl)cyclopropane-1-carboxylic acid esters, wherein the esters may be lower alkyl esters such as methyl, ethyl propyl or the like);
(e) a nucleic acid sequence of SEQ ID NO. 3
(f) a nucleic acid sequence coding for an amino acid sequence (SEQ ID NO: 12) comprising an amino acid sequence (SEQ ID NO: 13) encoded by the nucleic acid sequence of SEQ ID NO. 3 in which glycine at 160 is replaced with an amino acid selected from the group A) consisting of alanine, valine, leucine and serine, and glycine at 189 is replaced with an amino acid selected from the group B) consisting of alanine, valine, leucine, isoleucine, serine, threonine, phenylalanine, histidine, tyrosine and arginine; and (g) a nucleic acid sequence
hybridizing with the nucleic acid sequence as defined in (f) under stringent conditions, and
coding for an amino acid sequence which has the same activity as the amino acid sequence encoded by the nucleic acid sequence as defined in (f).

The nucleic acid sequence of SEQ ID NO. 1 can be obtained, for example, by preparing a cDNA library by a conventional method from *Aspergillus flavus* ATCC1 1492 strain and the like, and conducting PCR by using the cDNA library as a template.

The nucleic acid sequence of SEQ ID NO.2 can be obtained, for example, by preparing a cDNA from *Arthrobacter* SC-6-98-28 (FERM BP-3658, deposited under the Butapest Treaty as FERM BP-3658. The depositary institution was International Patent Organism Depositary (IPOD), formerly known as the National Institute of Bioscience and Human-Technology (NIBH)), and conducting PCR using the cDNA library as a template.

The nucleic acid sequence of SEQ ID NO.3 can be obtained, for example, by preparing a cDNA from *Chromobacterium* SC-YM-1, and conducting PCP using the cDNA library as a template. SC-YM-1 is deposited as FERM BP-6703, which had been originally deposited as FERM P-14009. The depositary institution is International Patent Organism Depositary (IPOD), formerly known as the National Institute of Bioscience and Human-Technology (NIBH).

Introduction of the site-specific mutations as described in item (g) above can be accomplished by preparing a mutated gene using a single stranded plasmid introduced with the original DNA, which is a wild type, as a template and a synthetic oligonucleotide containing a nucleotide sequence for introducing an appropriate mutation, as a primer. For example, methods of Smith et al. (Genetic Engineering 31 Setlow, J. and Hollaender, A Plenum: New York), Vlasuk et al. (Experimental Manupilation of Gene Expression, Inouye, M Academic Press, New York), Hos.N.Hunt et al. (Gene, 77, 51, 1989) and the like can be referred to.

In the present invention, PCR amplification can be conducted by using a mutation primer that is prepared so as to introduce substitutions of glycines at 160 and 189 with other amino acid as specified in groups A) and B) in item (g) above.

In the present invention, the DNA that hybridize with a certain DNA under stringent conditions means that (1) the DNA hybridizes with a certain DNA to form a DNA—DNA hybrid in a highly ionizing condition (e.g. 6×SSC (900 mM sodium chloride, 90 mM sodium citrate)) and at a temperature of 65° C., and (2) the formed hybrid is maintained even after keeping in a low ion concentration condition (e.g. 0.1×SSC (15 mM sodium chloride, 1.5 mM sodium citrate)) and at a temperature of 65° C. for 30 minutes in a Southern hybridization method. Regarding the Southern hydbridization, descriptions regarding the method in the following reference are referred to. For example, "Cloning and Sequence" (Supervised by Itaru Watanabe, Edited by Masahiro Sugiura, 1989, Published by Nosonbunkasha Co., Ltd.).

The transformed microorganisms used in the present method can be obtained, for example, from a DNA coding for an enzyme having a thermal denaturation temperature of 50° C. or higher and host microorganisms by a similar manner as described in "Molecular Cloning: A Laboratory Manual 2nd edition" (1989), Cold Spring Harbor Laboratory Press, and "Current Protocols in Molecular Biology" (1987), John Wiley & Sons, Inc. ISBNO-471-50338-X.

The transformed microorganisms obtained by the methods described above ore cultivated to express the introduced enzyme gene DNA and produce the enzymes useful for producing useful materials. The cultivation can be conducted according to a conventional method as described in the Principles of Fermentation Technology (1989), Japan Scientific Societies Press, P. F. Stanbury, A. Whitaker, Translated by Ayaaki Ishizaki.

The present method can be achieved by mixing at 25° C. or higher to less than 35° C. a solution of the transformed microorganism, obtained by the above methods, with at least one member selected from a group consisting of monovalent alcohols having one to three carbon atoms and acetone, in an amount of 10 to 35% by weight of the solution of the microorganism. The amount of the alcohols and acetone may be varied within the range described above, e.g. 10 to 30% by weight or 10 to 25% by weight.

Examples of the monovalent alcohols having one to three carbon atoms include, methanol, ethanol, n-proponol, iso-propanol.

Mixing of the solution containing the transformed microorganism of the *Escherichia* with at least one member selected from the group consisting of monovalent alcohols having one to three carbon atoms and acetone can be conducted, for example, by adding at least one and acetone can be conducted, for example, by adding at least one member selected from the group consisting of monovalent alcohols having one to three carbon atoms and acetone to the solution containing a transformed microorganism, and stirring the resulting mixture, or by simultaneously adding the solution containing the microorganism and at least one member selected from the group consisting of monovalent alcohols having one to three carbon atoms and acetone to a reactor under stirring or shaking.

The solution herein means that it is typically in a state of fluidity, and may be referred to a mixture or suspension solution of the microorganisms, and more particularly it usually means a cultivation solution containing the microorganisms, culture broth (solution), or diluted solutions thereof.

The stirring or shaking of the resulting mixture is conducted for an effective period of time so that the microorganisms are sterilized. The period is usually 5 minutes to 4 days, preferably 15 minutes to 2 days, more preferably 30 minutes to 2 days, further preferably 6 hours to 2 days, which is varied with the transformed microorganism density in the solution or suspension to be applied obtained after completion of the cultivation, the thermal denaturation temperature of the enzyme used, and/or the amount of the alcohols and acetone.

Completion of the sterilization of the microorganisms of the present method can be confirmed by the fact that no colony is formed on nutrient agar medium to which a portion of the treated mixture had been applied.

In the present method, the higher the thermal denaturation temperature of the enzyme is, the more amount of the alcohols and/or acetone can be added, thereby period of mixing the solution or suspension of the microorganism can be shortened accordingly.

The solution obtained by the present method can be used, for example, for synthetic organic reactions as it is or after treating the solution.

Examples of the treating include, for example, (1) a method of disrupting cells by treating sterilized cell solution with DYNO-Mill and removing the disrupted cells by a filtration film or a centrifugal separator, (2) a method of removing low molecular contents by ultrafiltration after removing the cells by a filtration film or a centrifugal separator, (3) a method of isolating the enzymes from the microorganism sterilized solution in a form of partially purified enzyme or purified enzyme, (4) a method of immobilizing the partially purified enzyme or purified enzyme isolated from the sterilized microorganism solution by a conventional method.

EXAMPLES

The present invention will be described below in more detail by means of production examples, but is not to be construed to limit the invention thereto.

Example 1

(1) 40 ml of a culture broth of E. coli JM105/pYHNK 2 strain obtained by the method described in the Reference 1 described below and 10 ml ethanol are added in a 100 ml glass vial and stirred for 24 hours at 30° C. Thereafter, the esterase activity of the mixed solution was found to be 95% or more of the culture broth (1) and the viable cell number was 0 cfu/ml.

Example 2

(1) 40 ml of a culture broth of E. coli JM105/pYHNK 2 strain obtained by the method described in the Reference 1 described below and 10 ml ethanol are added in a 100 ml glass vial and stirred for 6 hours at 30° C. Thereafter, the esterase activity of the mixed solution was found to be 95% or more of the culture broth (1) and the viable cell number was 0 cfu/ml.

Example 3

(1) 40 ml of a culture broth of E. coli JM105/pYHNK 2 strain obtained by the method described in the Reference 1 described 25 below and 10 ml ethanol are added in a 100 ml glass vial and stirred for 48 hours at 30° C. Thereafter, the esterase activity of the mixed solution was found to be 95% or more of the culture broth (1) and the viable cell number was 0 cfu/ml.

Example 4

(1) 42.5 ml culture broth of E. coli JM105/pYHNK 2 strain obtained by the method described in the Reference 1 and 7.5 ml ethanol are added in a 100 ml glass vial and stirred for 24 hours at 30° C. Thereafter, the esterase activity of the mixed solution was 95% or more of the culture broth (1) and the viable cell number was 0 cfu/ml.

Example 5

(1) 40 ml culture broth of E. coli JM105/pYHNK 2 strain obtained by the method described In the Reference 1 and 10 ml of methanol are added in a 100 ml glass vial and stirred for 24 hours at 30° C. Thereafter, the esterase activity of the mixed solution was 95% or more of the culture broth (1) and the viable cell number was 0 cfu/ml.

Example 6

(1) 40 ml culture broth of E. coli JM105/pYHNK 2 strain obtained by the method described in the Reference 1 and 10 ml of methanol are added in a 100 ml glass vial and stirred for 6 hours at 30° C. Thereafter, the esterase activity of the mixed solution was 95% or more of the culture broth (1) and the viable cell number was 0 cfu/ml.

Example 7

(1) 40 ml culture broth of E. coli JM105/pYHNK 2 strain obtained by the method described in the Reference 1 and 10 ml of methanol are 25 added in a 100 ml glass vial and stirred for 48 hours at 30° C. Thereafter, the esterase activity of the mixed solution was 95% or more of the broth solution (1) and the viable cell number was 0 cfu/ml.

Example 8

(1) 40 ml culture broth of E. coli JM105/pYHNK 2 strain obtained by the method described in the Reference 1 and 10 ml of methanol are added in a 100 ml glass vial and stirred for 5 hours at 25° C. Thereafter, the esterase activity of the mixed solution was 92% Y or more of the culture broth (1) and the viable cell number was 0 cfu/ml.

Example 9

(1) 40 ml culture broth of E. coli JM105/pYHNK 2 strain obtained by the method described in the Reference 1 and 10 ml of acetone are 10 added in a 100 ml glass vial and stirred for 24 hours at 30° C. Thereafter, the esterase activity of the mixed solution was 95% or more of the culture broth (1) and the viable cell number was 0 cfu/ml.

Example 10

(1) 40 ml culture broth of E. coli JM105/pYHNK 2 strain obtained by the method described in the Reference 1 and 10 ml of acetone are added in a 100 ml glass vial and stirred for 6 hours at 30° C. Thereafter, the esterase activity of the mixed solution was 95% or more of the culture broth (1) and the viable cell number was 0 cfu/ml.

Example 11

(1) 40 ml culture broth of E. coli JM105/pYHNK 2 strain obtained by the method described in the Reference 1 and 10 ml of acetone are added in a 100 ml glass vial and stirred for 48 hours at 30° C. Thereafter, the esterase activity of the mixed solution was 95% or more of the culture broth(1) and the viable cell number was 0 cfu/ml.

Example 12

(1) 40 ml culture broth of E. coli JM105/pYHNK 2 strain obtained by the method described in the Reference 1 and 6.5 ml of acetone are added in a 100 ml glass vial and stirred for 24 hours at 30° C. Thereafter, the esterase activity of the mixed solution was 95% or more of the culture broth (1) and the viable cell number was 0 cfu/ml.

Measurement of the enzyme activity in Examples 1 to 12 was conducted by the following method.

0.02 g of N-benzylazetidin-2-carboxyilic acid ethyl ester, 1.0 ml t-butyl methyl ether and 3.5 ml of 100 mM monopotassium phosphate-dipotassium phosphate buffer (pH 7.0) were added in a 10 ml threaded test tube and kept at 35' for 15 minutes. 200 $\mu$l of the esterase solution was put in the test tube to measure its esterase activity and shaken reciprocally (120 str/min) at 35° C. for 16 minutes. Then 400% 1 of the mixed solution was centrifuged (12000 rpm, 5 minutes) after 1 ml t-butyl methyl ether was added and stirred. 200 $\mu$l of the obtained aqueous phase was analyzed quantitatively (by absolute calibration curve method) with respect to N-benzylazetidin-2-carboxylic acid by high performance liquid chromatography after dissolved in 20 mM phosphate acid monopotassium water/acetonitrile=90/10 and filtered by a 0.2 $\mu$l filter.

Viable cell number in the Examples 1 to 12 was measured by the following methods.

The solution for measuring viable cell number was diluted with approximately 1 ml of saline pre-cooled to 4° C. 100 $\mu$l of the diluent was put on an LB agar plate (L-Broth Ager produced by BIO 101, Inc.) containing 100 µg/ml ampicillin and kept at 37° C. for 1 to 2 days. Then the viable cell number in the solution to be measured was calculated from a number of grown colonies.

The following describes Reference Example for producing culture solution used in the Examples.

Reference Example 1

A cDNA library was prepared according to a method described in "Bio General Catalog 1997/98 Vol. 1 Genetic Engineering E-24-27" from the *Aapergillus flavus* ATCC 1492 strain. PCR was performed (the Taq Polymerase Gold PCR kit produced by Perkin Elmer Kikotech, INC. was used) by using oligonucleotide shown in SEQ ID NO. 3 and SP Promoter primer (produced by Takara Shuzo Co., Ltd.) as a primer and the cDNA library described above as a template. PCR conditions are given below.

| Reaction Solution Composition | |
|---|---|
| cDNA library stock solution: | 1 µl |
| dNTP (2 mM-mix for each): | 10 µl |
| Primer (5 pmol/µl): | 1 µl, 2 kinds for each |
| 10x buffer (with MgCl): | 10 µl |
| Taq Polymerase Gold (2.5 U/µl): | 1 µl |
| Ultrapure water: | 76 µl |

PCR Condition;

A container containing the reaction mix solution was set in the GeneAmp PCR System 2400 (produced by Perkin Elmer, Inc.) and heat-treated at 98° C. for 7 minutes, then 20 cycles, of which single cycle consists of a treatment of 97° C. (0.3 minute), 45° C. (1 minute) and 72° C. (2 minutes), and further 20 cycles, of which single cycle consists of a treatment of 94° C. (1 minute), 50° C. (0.3 minute) and 72° C. (2 minutes), were performed and then the solution was treated at 70° C. for 7 minutes.

The DNA thus obtained having the nucleic acid sequence shown in SEQ ID NO. 1 was ligated on the PCR Product insertion site of the PCR2.1-TOPO Vector attached to the TOPOTMTA cloning kit Ver. E kit (produced by Invitrogen Corporation) to obtain a vector pYHNK1.

The ligation reaction solution was added to the *E. coli* JM 105 competent cell (produced by Pharmacia Biotech, Inc.) to obtain transformed microorganisms introduced with the vector pYHNK1 produced by the ligation reaction. The transformed microorganisms were cultivated to prepare a large amount of vector pYHNK1 by using the QIAGEN plasmid kit (produced by QIAGEN, Inc.) according to the protocol accompanied to the kit.

Oligonucleotide AF1 and oligonucleotide AR2, and oligonucleotide AF2 and oligonucleotide AR3 shown in Table 1 were respectively annealed by keeping at 90° C. for 5 minutes to obtain double stranded DNAs. Two kinds of the obtained double stranded oligonucleotide and the pTV118N (produced by Takara Shuzo Co., Ltd.) cut and opened previously by NcoI and EcoRI were connected with each other by using the ligation kit (produced by Takara Shuzo Co., Ltd.) to produce secretion vector (hereinafter, refer to secretion vector A). Amino acid sequence coded in the linker region inserted in the secretion vector is described in SEQ ID NO. 2.

TABLE 1

| Oligonucleotide | Sequence |
|---|---|
| AF1 | CATGAAACAAAGCACTATTGCACTGGCACTC |
| SEQ ID NO: 6 | TTACCGTTACTGTTTACCCCTGTGGCAAACG |
| AF2 | CAGCGCCGACCAGCAACCCGGCACAGGAACT |
| SEQ ID NO: 7 | GG |
| AR2 | AAACAGTAACGGTAAGAGTGCCAGTGCAATA |
| SEQ ID NO: 8 | GTGCTTTGTTT |
| AR3 | AATTCCAGTTCCTGTGCCGGGTTGCTGGTCG |
| SEQ ID NO: 9 | GCGCTGCGTTTGCCACAGGGGT |

Then, plasmid pYHNK2 was obtained by inserting DNA fragment (approximately 800 bp) excised from the vector pYHNK1 by the EcoRI into an EcoRI site of the above secretion vector A. The transformant *E. coli* JM105/pYHNK2 strain into which plasmid pYHNK2 has been introduced was obtained by adding the reaction solution containing the plasmid pYHNK2 obtained as shown above to the *E. coli* JM 105 competent cell (produced by Pharmacia Biotech, Inc.) to select by using the LB agar media (L-broth powder (produced by Takara Shuzo Co., Ltd.)) containing 100 µg/ml ampicillin.

A 10 ml liquid medium (5 g glycerol, 6 g yeast extract, 4 g monopotassium phosphate and 9.3 g dipotassiumphosphate acid are dissolved in 1 liter of water) was added in a test tube and sterilized. Ampicillin was added thereto so that the concentration thereof was 50 µg/ml, and additionally, 0.1 ml glycerol stock of the *E. coli* JM105/pYHNK2 strain was added and cultured under shaking at 30° C. for 9 hours. A 1500 ml liquid medium (22.5 g of glycerol, 15 g of yeast extract 22.5 g of SogoominosanF®, 6 g of monopotassium phosphate, 3.6 g of magnesium sulfate, 0.06 g of ferric sulfate heptahydrate and 0.06 g of calcium chloride dihydrate are dissolved in 1500 ml water, of which pH was adjusted to pH7.0 by adding 4M aqueous phosphate solution and 14% (w/w) aqueous ammonia) is added in 3 liter jar fermenters and sterilized, Ampicillin was added thereto to be 50 µg/ml and additionally 0.75 ml of the culture solution cultured in the above test tube was added and aerobically cultured under stirring at 30° C. After 18 hours from starting cultivation, isopropyl thio β-D-galactoside (IPTG) was added thereto so that the concentration thereof was 50 µM. After 14 hours from starting cultivation, a sterilized culture medium (150 g of glycerol, 28 g of yeast extract and 42 g of SogoaminosanF® were dissolved in 110 g water) was added gradually during cultivation. The culture broth (1) was obtained by cultivation of 40 hours after starting cultivation.

Reference Example 2

500 ml of the cultivation solution obtained in Reference Example 1 above was subjected to centrifugation to give microorganism cells, which was then suspended in the 300 ml of 100 mM monopotassium phosphate-dipotassium phosphate buffer (pH 7.0) and milled using DYNO-MILL (WILLY A. BACHOFEN AG, Glass beads, 0.1 to 0.2 mm φ3000 rpm, 30 minutes). The resulting cell suspension was subjected to centrifugation to give a supernatant crude enzyme solution. 50 ml of the crude enzyme solution was purified with weak ion-exchange chromatography (column: DEAE Sepharose FF (30 ml), Buffer A: 10 mM Tris (hydroxymethyl)aminometane(Tris))-hydrochoride buffer solution, pH 7.0 (300 ml), Buffer B: 10 mM Tris-hydrochloride buffer solution, pH 7.0, 0.1 M NaCl (300 ml), flow rate: 4 ml/min) to obtain a fraction having the enzyme activity. The obtained fraction was concentrated and applied onto gel filtration chromatography (column: HiLoad 16/60 Superdex g 200 (120 ml), Buffer A: 10 mM Tris-hydrochloride buffet, pH 7.0, 0.2 M NaCl, flow rate: 1 ml/min) to obtain a fraction having the enzyme activity. The obtained was purified with a strong anion-exchange column chromatography (column: Hitrap Q (1 ml), Buffer A: 10 mM Tris-hydrochloride buffer(pH 7.0, 30 ml), Buffer B: 10 mM Tris-hydrochloride buffer(pH 7.0, 1 M NaCl, (30 ml) flow rate: 1 ml/min) to give a fraction having the esterase activity. The obtained esterase fraction was revealed to be a single band by the SDS-PAGE analysis. The purified fraction was used as the purified enzyme.

The thermal denaturation temperature of the purified enzyme was measured by circular dichroism spectrum. Circular dichrosim photometer J-720(manufactured by Nippon Bunko, Company, Limited was used to measure circular dichroism spectrum of 5 µg/ml of the purified enzyme (10 mM sodium phosphate buffer (pH 7) obtained as above at a temperature range of from 30 to 70° C. and with a temperature slope of 50° C. hour using a wavelength of 222 nm. It was found from the thermal denaturation curve obtained from circular dichrosim spectrum that the thermal denaturation temperature of the purified enzyme was 53.1° C.

Reference Example 3

1.0 g of N-benzylazetidin-2-carboxylic acid ethyl ester, 0.56 g of 25 heptane and 1.2 g of distilled water were put in a sample vial, to which was added 0.06 g of the mixed solution obtained in the Example 2 and stirred at 10° C. for 24 hours. Then, the reaction solution was centrifuged (10000 rpm, 10 minutes) and the obtained water phase was analyzed to find that N-benzylazetidin-2-carboxylic acid had been formed in 49% yield based on the N-benzylazetidin-2-carboxylic acid ethyl used in the reaction.

Example 13

45 g of the culture broth of E. coli JM 10/pEAR5 strain (2) obtained by the method in the Reference Example 5 as described below and 5 g of ethanol were added to a 100 ml glass vial, and stirred for 24 hours at 30° C. Thereafter, the esterase activity of the solution was found to be 95% or more of the culture broth (2), and the viable cell 10 number was found to be 0 cfu/ml.

Example 14

37.5 g of the culture broth of E. coli JM105/pEAR6 strain (2) obtained by the method in the Reference Example 5 as described below and 12.5 g of ethanol were added to a 100 ml glass vial, and stirred for 24 hours at 30° C. Thereafter, the esterase activity of the solution was found to be 95% or more of the culture broth (2), and the viable cell number was found to be 0 cfu/ml.

Measurement of the Esterase Activity in Example 13 and 14:

To 5 ml of a diluted solution of the culture broth or sterilized solution obtained by the pre sent method was added 1 g of 2,2-dichloro-3-(1-propenyl)cyclopropane-1-carboxylic acid methyl ester (1R/1S=50/50, trans/cis98/2) and the resulting mixture was stirred at 45° C. for 30 minutes while maintaining the pH at 10.0. A portion of the reaction solution was sampled, acidified with hydrochloric acid, and extracted with ethyl acetate. The extract solution was analyzed by gas-chromatography to measure the hydrolysis rate (Internal standard: methyl cinnamate, column: HR20M 0.53 φ, 30 m, 1 µ, ULBON). The esterase activity was calculated from the hydrolysis rate.

Example 15

45 g of the culture broth of E. coli JM 105/pCC16OS189Y363term strain, disclosed in JP7-213280A, referred to as (3), obtained by the method in the Reference Example 6 as described below and 5 g of ethanol were added to a 100 ml glass vial, and stirred for 24 hours at 30° C. Thereafter, the esterase activity of the solution was found to be 95% or more of the culture broth (3), and the viable cell number was found to be 0 cfu/ml.

Example 16

37.5 g of the culture broth of E. coli JM 105/pCC 160S189Y363term strain (3) obtained by the method in the Reference Example 6 as described below and 12.5 g of ethanol were added to a 100 ml glass vial, and stirred for 24 hours at 30° C. Thereafter, the esterase activity of the solution was found to be 95% or more of the culture broth (3), and the viable cell number was found to be 0 cfu/ml.

Measurement of the Enzyme Activity in Examples 15 to 16

Measurement of the enzyme activity was performed by using p-nitrophenyl acetate (pNPA) as a substrate. A sample enzyme solution was added to a 3.0 ml of 100 mM phosphate buffer solution (pH 7.5) containing the substrate at a concentration of 5 mM and the resulting mixture is maintained at 37° C. An amount of liberated p-nitrophenol was measured by the increase of absorbance at 405 nm.

Number of viable cells was determined by the following method.

About 1 ml of a sample solution to be measured with the number of viable cells was diluted with physiological saline cooled to 4° C. 100 µl of the diluted solution was applied onto a LB-medium plate (L-Broth Ager (manufactured by BIO 101 Company, Ltd) containing ampicilline at a concentration of 100 µ/ml and kept at 37° C. for 1 to 2 days. Thereafter, number of the viable cells was calculated from the number of colonies grown thereon.

Reference Example 4

E. coli JM105/pEAR5 strain introduced with an esterase derived from Arthrobacter SC-6-98-28 was prepared according to a method as disclosed in JP5-56787A. Plasmid pAGE-1 disclosed in JP5-56787A was digested with restriction enzymes Nsp(7524)V and HindIII to cut out a DNA fragment containing a coding region of the esterase. The obtained fragment was ligated with a DNA fragment which was prepared to convert the initiation codon and proximity regions thereof, and a digested product of an expression vector pUC118 containing lac promoter (Takara Shuzo Company, Limited) digested with restriction enzymes BamHI and HindIII, as disclosed in JP5/56787A. Thus, an expression plasmid for E. coli containing a gene coding for the esterase derived from Arthrobacter SC6-98-28 strain located downstream of the lac promoter was prepared and introduced into E. coli JM 105 strain.

Reference Example 5

10 ml of L-Broth medium (manufactured by Sigma Company, Limited) was added in a test tube and sterilized. Ampicillin was added thereto so as to be 50 µg/ml, to which was added 0.1 ml of a glycerol stock of E. coli JM105/pEAR5 strain, and incubated at 30° C. for 16 hours under shaking.

10 ml of L-Broth medium (manufactured by Sigma Company, Limited) was added in a 500 ml Erlenmeyer flask equipped with baffles, and sterilized. Ampicilline was added thereto so that the concentration thereof was 50 µg/ml, and 1 ml of the cultivation solution in the test tube prepared as above was also added thereto, and incubated under stirring at 30° C. After 4 hours, IPTG was added thereto so that the concentration thereof was 1 mM. After 24 hours from the beginning of the incubation, the culture broth (2) was obtained.

Reference Example 6

E. coli JM 105/pCC 160S189Y363term strain introduced with a gene coding for an esterase derived from Chromobacterium SC-YM-1 used in the Example above was prepared according to the method as disclosed in JP7-213280A. The esterase produced by E. coli JM105/pCC160S189Y363term strain is a thermo-stable esterase introduced with mutations which substitute an amino acid at 160 with serine and an amino acid at 189 with tyrosine in the amino acid sequence, which is shown together with the polynucleotide sequence of SEQ ID NO.3, encoded by the polynucleotide sequence of SEQ ID NO.3.

Reference Example 7

10 ml of L-Broth medium (manufactured by Sigma Company, Limited) was added in a test tube and sterilized. Ampicillin was added thereto so that the concentration thereof was 50 µg/ml, to which was added 0.1 ml of a glycerol stock of E. coli JM105/pCC160S189Y363term strain, and incubated at 30° C. for 16 hours under shaking.

10 ml of L-Broth medium (manufactured by Sigma Company, Limited) was added in a 500 ml Erlenmeyer flask equipped with baffles, and sterilized. Ampicilline was added thereto so that the concentration thereof was 50 µg/ml, and 1 ml of the cultivation solution in the test tube prepared as above was also added thereto, and incubated under stirring at 30° C. After 4 hours, IPTG was added thereto so that the concentration thereof was 1 mM. After 12 hours from the beginning of the incubation, the culture broth (3) was obtained.

Example of the measurement of a thermal denaturation temperature of the esterase derived from Arthrobacter SC-&98-28 used in the Examples is shown below.

Reference Example 8

100 ml of liquid medium, prepared by dissolving 5 g of glycerol, 6 g of yeast extract 9 g of potassium phosphate, and 4 g of dipotassium phosphate in 1 l of water and pH thereof was adjusted to 7, was added to a 500 ml Erlenmeyer flask and sterilized. Thereafter, ampicilline was added thereto so as to be 50 µg/ml and inoculated with a loop of E. coli JM105/pEAR5 strain on the slant culture, and incubated at 30° C. for 24 hours under reciprocally shaking. 1500 ml of sterilized liquid medium, prepared by dissolving 15 g of glycerol, 25 g of yeast extract, 0.4 g of monopotassium phosphate, 2 g of magnesium sulfate and 0.1 g of ferric sulfate in 1l 1 of water, and pH thereof was adjusted to pH 7, was added to a 3l jar fermentor (manufactured by Marubishi Bioengi, Ltd, MDL type), and inoculated with 15 ml of the cultivation solution prepared as above. Cultivation thereof was conducted aerobically under stirring at 30° C. and IPTG was added during logarithmic phase, 10 to 15 hours after the initiation of the cultivation, so that the concentration thereof was 1 mM. Then sterilized cultivation medium was poured thereto and incubated for 40 hours to give the culture broth. 2000 ml of the culture broth obtained as above was subjected to centrifugation to give microorganism cells, which were washed with water and suspended in 50 mM of Tris-hydrochloride buffer (pH 8.0) to give a 1000 ml suspension solution. The suspension was ultrasonicated in ice-water to give a disrupted cell-solution, and supernatant was obtained from the solution by centrifugation (10000 rpm, 30 minutes). Sodium chloride was added thereto so that the concentration thereof was 1 M, and heat-treated at 60° C. for 30 minutes. Therafter a supernatant was obtained by centrifugation (10000 rpm, 30 minutes). To the supernatant was added 35% saturated ammonium sulfate, and centrifugated again to obtain precipitions. The obtained precipitates were dissolved in about 50 ml of 20 mM Tris-hydrochloride buffer(pH 8.0) and was dialyzed with 200 times by volume of 20 mM Tris-hydrochloride buffer (pH 8.0) containing 0.1 M NaCl. The dialyzed solution was subjected to centrifugation to give a supernatant, which was purified with an anion-exchange column chromatography (column: DEAE Spherarose fast flow (diameter: 26 mm, length: 400 mm), Buffer A: 20 mM Tris-hydrochloride buffer(pH 8.0, 200 ml) containing 0.1 M NaCl, Buffer B: 20 mM Tris-hydrochloride buffer (pH 8.0, 200 ml) containing 0.6M NaCl, flow rate: 12 ml/min) to give a fraction having the esterase activity. The obtained esterase fraction was revealed to be a single band by the SDS-PAGE analysis, but was found to have a minor band by silver stain. Therefore, the fraction was further subjected to fractgel-EMAE (column: superperformance column (diameter: 10 mm, length: 150 mm), Bed: fractogel-TMAE EMD 650 (S), manufactured by Merck, Ltd, Buffer A: 20 mM Tris-hydrochloride buffer (pH 8.0), Buffer B: 20 mM Tris-hydrochloride buffer(pH 8.0, 200 ml) containing 1.0 M NaCl, flow rate: 1.5 ml/min)) to obtain a fraction having the esterase activity which fraction was used as the purified enzyme.

The thermal denaturation temperature of the purified enzyme was measured by circular dichroism spectrum. Circular dichrosim photometer J-720(manufactured by Nippon Bunko, Company, Limited was used and Circular dichroism spectrum of 40 µg/ml of the purified enzyme (10 mM sodium phosphate buffer (pH 7.5) obtained as above was measured at a temperature range of from 40 to 80° C. and with a temperature slope of 20%/hour using a wavelength of 222 nm. It was found from the thermal denaturation curve obtained from circular dichrosim spectrum that the thermal denaturation temperature of the purified enzyme was 67.0° C.

Reference Example 9

Thermal denaturation temperature of an esterase derived from ChromobacteriumSC-YM-1 strain, E. coli JM105/pCC160S189Y363term strain, was observed in a following manner.

A cultivation medium was prepared by adding thiamine and ampicilline to 50 ml of M9 cultivation medium (2 mM magnesium sulfate, 0.1 mM calcium chloride, 5 g/L glucose, 3.4 g/L sodium hydrogenphosphate, 0.67 g/L monopotassium phosphate, 0.22 g/L ammonium chloride, 0.11 g/L sodium chloride, pH 7.0) charged in a 200 ml Erlenmeyer flask so that the concentration thereof was 2.0 mg/L and 50 µg/ml respectively. A loop of E. coli JM105/pCC160S189Y396term strain, which has been grown on a plate containing the same ingredients as the cultivation medium prepared above, was inoculated to the prepared medium and cultivated at 37° C. for 12 hours under stirring. 3 ml of the obtained cultivation solution was inoculated to a liquid medium prepared by sterilizing 300 ml of liquid medium in a 2000 ml Erlenmeyer flask, which medium had been prepared by dissolving 4 g of glycerol, 24 g of yeast extract, 12 g of tripton, 2.3 g of monopotassium phosphate, and 12.5 g dipotassium phosphate in 1 L of water, adjusting pH to 7.0, and ampicillin was added thereto so that the concentration thereof was 50 µg/ml. Incubated at 37° C. under shaking. When the OD 660 reached at 2, IPTG was added so as to make its concentration 0.1 mM, and further cultivated for 6 hours to obtain a culture broth.

The obtained culture broth was subjected to centrifugation to give about 43 g of wet cells. The wet cells were washed with TE buffer (pH 7.5) and suspended in the same buffer solution so as to make OD 660 thereof to be 60. The suspended cell were ultrasonically disrupted in ice-water, and subjected to centrifugation (3200 g, 10 min, then 110000 g, 60 min) to give a supernatant, which was concentrated with a ultrafiltration membrane to give a 50 ml of a concentrated solution. The concentrated solution was purified with an anion-exchange chromatography (column: DEAE Sepharose fast flow (diameter 26 mm, length 320 mm), Buffer A: 10 mM Tris-hydrochloride buffer solution containing 0.15 M NaCl, pH 7.5 (500 ml), and Buffer B: 10 mM Tris-hydrochloride buffer solution containing 0.35 M NaCl, pH 7.5 (500 ml), flow rate: 3 ml/min) to obtain a fraction having the esterase activity. The fraction was applied onto hydrophobic chromatography (column: Butyltoyopearl 650S(diameter: 16 mm, length: 300 mm), Buffer A: 10 mM Tris-hydrochloride buffer solution containing 10% ammonium sulfate, pH 7.5 (200 ml), Buffer B: 10 mM Tris-hydrochloride buffer, pH 7.5 (200 ml), flow rate: 2 ml/min) to obtain a fraction having the enzyme activity. This fraction was used as a purified enzyme fraction.

The thermal denaturation temperature of the purified enzyme was measured by circular dichroism spectrum. Circular dichrosim photo-meter J-720(manufactured by Nippon Bunko, Company, Limited was used to measure circular dichroism spectrum of 4 μg/ml of the purified enzyme (10 mM sodium phosphate buffer (pH 7.5) obtained as above at a temperature range of from 30 to 70° C. and with a temperature slope of 20° C./hour using a wavelength of 222 nm. It was found from the thermal denaturation curve obtained from circular dichrosim spectrum that the thermal denaturation temperature of the purified enzyme was 62.6° C. In addition, the thermal denaturation temperature of the wild type esterase of Chromobacterium SC-YM-1 strain was 50.5° C.

Effects of the Invention

According to the present invention, transformed microorganisms introduced with genes coding for an enzyme to be used for producing useful materials can be sterilized without inaction of the enzyme activities, which was produced by the transformed microorganisms and can be used for producing useful materials.

What is claimed is:

1. A method for preventing a transformed microorganism from multiplying, which comprises mixing at a temperature range of from 25° C. to less than 35° C. a solution containing a transformed microorganism belonging to *Escherichia* said microorganism having been transformed by introducing a DNA coding for an enzyme having a thermal denaturation temperature of 50° C. or higher, with at least one member selected from the group consisting of mono-hydroxy alcohols having one to three carbon atoms and acetone, in an amount of 10 to 35% by weight of the solution.

2. A method according to claim 1, wherein the enzyme is a hydrolase.

3. A method according to claim 1, wherein the enzyme is an enzyme having a thermal denaturation temperature of 60° C. or higher.

4. A method according to claim 1, wherein the enzyme is an enzyme having a thermal denaturation temperature of 53° C. or higher and the amount of the at least one member selected from mono-hydroxy alcohols and acetone is 10% to 30% by weight.

5. A method according to claim 1, wherein the amount of at least one member selected from mono-hydroxy alcohols and acetone is from 10% to 25% by weight.

6. A method according to claim 1, wherein the DNA has
   1) a nucleic acid sequence of SEQ ID NO: 1,
   2) a nucleic acid sequence of SEQ ID NO: 2,
   3) a nucleic acid sequence of SEQ ID NO: 3, or
   4) a nucleic acid sequence:
      hybridizing with the nucleic acid sequence of SEQ ID NO: 1, 2, or 3 under high stringent conditions, and coding for an enzyme having the same activity as the enzyme encoded by the nucleic acid sequence of SEQ ID NO: 1, 2, or 3.

7. A method according to claim 1, 2, 4 or 5, wherein the DNA has:
   1) a nucleic acid sequence of SEQ ID NO: 1, or
   2) a nucleic acid sequence:
      hybridizing under high stringent conditions with the nucleic acid sequence of SEQ ID NO: 1, and
      coding for an amino acid sequence of an enzyme capable of asymmetrically hydrolyzing a racemic N-benzylazetidin-2-carboxylic acid ethyl ester to produce (S)-N-benzylazetidin-2-carboxylic acid.

8. A method according to claim 1, 2 or 4, wherein the DNA has:
   1) a nucleic acid sequence of SEQ ID NO: 2, or
   2) a nucleic acid sequence:
      hybridizing under high stringency conditions with the nucleic acid sequence of SEQ ID NO: 2, and
      coding for an amino acid sequence of an enzyme capable of asymmetrically hydrolyzing a chrysanthemic acid ester derivative.

9. A method according to claim 1, 2 or 3, wherein the DNA has:
   1) a nucleic acid sequence of SEQ ID NO: 3,
   2) a nucleic acid sequence coding for an amino acid sequence comprising an amino acid sequence encoded by the nucleic acid of SEQ ID NO: 3 in which
      glycine at 160 is replaced with an amino acid selected from the group A consisting of alanine, valine, leucine and serine, and
      glycine at 189 is replaced with an amino acid selected from the group B consisting of alanine, valine, leucine, isoleucine, serine, threonine, phenylalanine, histidine, tyrosine and arginine, or
   3) a nucleic acid sequence
      hybridizing with the nucleic acid sequence as defined in 2) under high stringent conditions, and
      coding for an amino acid sequence which has the same activity as the amino acid sequence encoded by the nucleic acid sequence as defined in 2).

10. A method according to claim 1, wherein the microorganism is a microorganism belonging to *Escherichia coli*.

11. A process for producing an enzyme solution, which comprises mixing at a temperature range of from 25° C. to less than 35° C. a solution containing a transformed microorganism belonging to *Escherichia*, said microoganism having been transformed by introducing a DNA coding for an enzyme having a thermal denaturation temperature of 50° C. or higher, with at least one member selected from the group consisting of mono-hydroxy alcohols having one to three carbon atoms and acetone, in an amount of 10 to 35% by weight of the solution, and recovering the enzyme solution.

12. A composition of an expressed enzyme produced by a transformed microorganism belonging to *Escherichia*, said microorganism having been transformed by introducing a DNA coding for an enzyme having a thermal denaturation temperature of 50° C. or higher, which comprises an enzyme solution produced by
   (a) mixing at a temperature range of from 25° C. to less than 35° C. a solution containing a transformed microorganism belonging to *Escherichia*, said microorganism having been transformed by introducing a DNA coding for an enzyme having a thermal denaturation temperature of 50° C. or higher, with at least one member selected from the group consisting of mono-hydroxy alcohols having one to three carbon atoms and acetone, in an amount of 10 to 35% by weight of the solution.

13. A method according to claim 1, wherein the at least one member is selected from the group consisting of methanol, ethanol and acetone.

14. A method according to claim 11, wherein the member is at least one of methanol, ethanol or acetone.

15. A method according to claim 1, wherein said mixing is conducted at a temperature range of 25° C. to 30° C.

16. A method according to claim 1, wherein said enzyme is an esterase.

17. A composition of an expressed enzyme produced by a transformed microorganism belonging to *Escherichia*, said microorganism having been transformed by introducing a DNA coding for an enzyme having a thermal denaturation temperature of 50° C. or higher, which composition comprises an enzyme solution produced by
   (a) mixing at a temperature range of from 25° C. to less than 35° C. a solution containing a transformed microorganism belonging to *Escherichia*, said microorganism having been transformed by introducing a DNA coding for an enzyme having a thermal denaturation temperature of 50° C. or higher, with at least one member selected from the group consisting of alcohols having one to three carbon atoms and acetone, in an amount of 10 to 35% by weight of the solution, and
   (b) recovering the enzyme solution by filtration, centrifugation, or ultrafiltration.

* * * * *

SEQUENCE LISTING

<160> NUMBER OF SEQ ID NOS: 13

<210> SEQ ID NO 1
<211> LENGTH: 798
<212> TYPE: DNA
<213> ORGANISM: Aspergillus flavus
<220> FEATURE:
<221> NAME/KEY: CDS
<222> LOCATION: (1)..(768)

<400> SEQUENCE: 1

```
atg cat ctt cct atc aag act ctc ttt gtc tct ctc ctc gga gcc agc      48
Met His Leu Pro Ile Lys Thr Leu Phe Val Ser Leu Leu Gly Ala Ser
  1               5                  10                  15 gtt ctc gca cgc cct ctt ccc aat gat gct ctc gtt gag aga aac gct      96
Val Leu Ala Arg Pro Leu Pro Asn Asp Ala Leu Val Glu Arg Asn Ala
             20                  25                  30 ccc cta aac gag ttc ctc agc gtc ctt ctg tct cat ttg cct gcc att     144
Pro Leu Asn Glu Phe Leu Ser Val Leu Leu Ser His Leu Pro Ala Ile
         35                  40                  45 aac ggc tct atc act gcg gtg tcg ggt ctg atc acc gat ttt gat caa     192
Asn Gly Ser Ile Thr Ala Val Ser Gly Leu Ile Thr Asp Phe Asp Gln
     50                  55                  60 ttg ctt gct gac atc acc ggt gct caa aca acc ctg aat gga ttt act     240
Leu Leu Ala Asp Ile Thr Gly Ala Gln Thr Thr Leu Asn Gly Phe Thr
 65                  70                  75                  80 ggt gcc tgc acg gat tac acc gtt ctc ttc gcc cgc gga acc agt gag     288
Gly Ala Cys Thr Asp Tyr Thr Val Leu Phe Ala Arg Gly Thr Ser Glu
                 85                  90                  95 ccc gga aac gtt ggt gtc ctc gtc gga cct cct ctt gct gag gcg ttt     336
Pro Gly Asn Val Gly Val Leu Val Gly Pro Pro Leu Ala Glu Ala Phe
            100                 105                 110 gag gga gcc gtc ggt gcg tcc gcc ttg agc ttc cag ggt gtc aac ggc     384
Glu Gly Ala Val Gly Ala Ser Ala Leu Ser Phe Gln Gly Val Asn Gly
        115                 120                 125 tat tct gca tct gtc gag gga tat ttg gct gga ggt gaa gcc gct ggc     432
Tyr Ser Ala Ser Val Glu Gly Tyr Leu Ala Gly Gly Glu Ala Ala Gly
    130                 135                 140 agc aag gca atg gca tct cag gcc agc gac att ctc tcc aag tgt ccc     480
Ser Lys Ala Met Ala Ser Gln Ala Ser Asp Ile Leu Ser Lys Cys Pro
145                 150                 155                 160
```

```
gac acc aag ctt gtc atg agt ggc tat tcc cag ggc tgc cag att gtt      528
Asp Thr Lys Leu Val Met Ser Gly Tyr Ser Gln Gly Cys Gln Ile Val
            165                 170                 175 cac aat gcc gtt gag caa ctt cct gcg gaa cac gca agc aag atc agc      576
His Asn Ala Val Glu Gln Leu Pro Ala Glu His Ala Ser Lys Ile Ser
        180                 185                 190 agc gtc ctc ctt ttc gga gac cca tac aag ggc aag gct ctc ccc aac      624
Ser Val Leu Leu Phe Gly Asp Pro Tyr Lys Gly Lys Ala Leu Pro Asn
    195                 200                 205 gtt gat gct tcc cgc gtc cac act gtg tgc cac gct gga gac act att      672
Val Asp Ala Ser Arg Val His Thr Val Cys His Ala Gly Asp Thr Ile
210                 215                 220 tgc gag aac agc gtt att att ctg ccc gct cac ttg acc tac gct gtt      720
Cys Glu Asn Ser Val Ile Ile Leu Pro Ala His Leu Thr Tyr Ala Val
225                 230                 235                 240 gat gtg gct tct gcg gct gac ttc gct gtt gcg gct gca aag aac taa      768
Asp Val Ala Ser Ala Ala Asp Phe Ala Val Ala Ala Ala Lys Asn
                245                 250                 255 attacgataa gggctccatg ttcactgtaa                                     798

<210> SEQ ID NO 2
<211> LENGTH: 1125
<212> TYPE: DNA
<213> ORGANISM: Arthrobacter globiformis
<220> FEATURE:
<221> NAME/KEY: CDS
<222> LOCATION: (1)..(1125)

<400> SEQUENCE: 2 gtg gat gca cag acg att gcc cct gga ttc gaa tca gtc gcc gaa ctc       48
Val Asp Ala Gln Thr Ile Ala Pro Gly Phe Glu Ser Val Ala Glu Leu
1               5                   10                  15 ttt ggc cgt ttc ctg agc gaa gac cgg gaa tat tca gcc cag ctc gcg       96
Phe Gly Arg Phe Leu Ser Glu Asp Arg Glu Tyr Ser Ala Gln Leu Ala
            20                  25                  30 gcc tac cac cgc gga gtc aag gta ttg gac atc agc ggt ggg ccg cac      144
Ala Tyr His Arg Gly Val Lys Val Leu Asp Ile Ser Gly Gly Pro His
        35                  40                  45 cgc cgc ccg gat tcc gtg acc ggt gtt ttc tcc tgc tcc aag gga gta      192
Arg Arg Pro Asp Ser Val Thr Gly Val Phe Ser Cys Ser Lys Gly Val
    50                  55                  60 tcc ggg ctg gtc atc gca ctt ttg gtc cag gac ggc ttc ctc gac ctc      240
Ser Gly Leu Val Ile Ala Leu Leu Val Gln Asp Gly Phe Leu Asp Leu
65                  70                  75                  80 gac gcc gaa gtg gtc aag tac tgg ccg gaa ttc ggc gcc gaa gga aag      288
Asp Ala Glu Val Val Lys Tyr Trp Pro Glu Phe Gly Ala Glu Gly Lys
                85                  90                  95 gcc acg att acc gtg gcc cag ctg ctc tcc cac cag gcc ggg ctt ctg      336
Ala Thr Ile Thr Val Ala Gln Leu Leu Ser His Gln Ala Gly Leu Leu
            100                 105                 110 gga gtc gaa ggc gga ctc acc ctc gcg gaa tac aac aac tcc gaa ctg      384
Gly Val Glu Gly Gly Leu Thr Leu Ala Glu Tyr Asn Asn Ser Glu Leu
        115                 120                 125 gcc gcc gcc aag ctc gcg cag atg cgg ccg ctg tgg aag ccc ggg acc      432
Ala Ala Ala Lys Leu Ala Gln Met Arg Pro Leu Trp Lys Pro Gly Thr
    130                 135                 140 gcc ttc ggg tac cac gcc ctg acc atc ggc gtc ttc atg gag gag ctt      480
Ala Phe Gly Tyr His Ala Leu Thr Ile Gly Val Phe Met Glu Glu Leu
145                 150                 155                 160 tgc cgc cgg atc acc ggg tcc acg ctc cag gaa atc tac gaa cag cgg      528
```

-continued

```
                Cys Arg Arg Ile Thr Gly Ser Thr Leu Gln Glu Ile Tyr Glu Gln Arg
                                165                 170                 175 atc cgc tcg gtc acg ggc gcc cac ttc ttc ctg gga ctg cct gag tcc        576
Ile Arg Ser Val Thr Gly Ala His Phe Phe Leu Gly Leu Pro Glu Ser
            180                 185                 190 gag gaa ccc cgc tat gcc acc ctc cgt tgg gct gca gac ccc tcc cag        624
Glu Glu Pro Arg Tyr Ala Thr Leu Arg Trp Ala Ala Asp Pro Ser Gln
        195                 200                 205 ccg tgg att gat ccc gcc agc cat ttc ggc ctt tcc gca aac tcg gcc        672
Pro Trp Ile Asp Pro Ala Ser His Phe Gly Leu Ser Ala Asn Ser Ala
    210                 215                 220 gtg ggg gac atc ctt gac ctg ccc aac ctc cgc gag gtc cgc gca gcc        720
Val Gly Asp Ile Leu Asp Leu Pro Asn Leu Arg Glu Val Arg Ala Ala
225                 230                 235                 240 ggc ctg agt tca gcc gcc gga gtc gcc agc gcg gaa ggc atg gcc cgc        768
Gly Leu Ser Ser Ala Ala Gly Val Ala Ser Ala Glu Gly Met Ala Arg
                245                 250                 255 gtc tac gct gcg gca ctc acc gga ctt gcc gcc aac ggc gac cga gcc        816
Val Tyr Ala Ala Ala Leu Thr Gly Leu Ala Ala Asn Gly Asp Arg Ala
            260                 265                 270 gcc gtc gcg ccc ctc ctc agc gaa gag acc atc caa acc gtc acg gcc        864
Ala Val Ala Pro Leu Leu Ser Glu Glu Thr Ile Gln Thr Val Thr Ala
        275                 280                 285 gag cag gtc ttc ggc atc gac cgg gtg ttc ggc gag acg agc tgc ttt        912
Glu Gln Val Phe Gly Ile Asp Arg Val Phe Gly Glu Thr Ser Cys Phe
    290                 295                 300 ggg aca gtg ttc atg aaa tcg cat gca cgc tcg cct tat ggc agc tac        960
Gly Thr Val Phe Met Lys Ser His Ala Arg Ser Pro Tyr Gly Ser Tyr
305                 310                 315                 320 cgg gcg ttc ggg cac gac ggc gcc agc gca tct ttg ggg ttc gct gac       1008
Arg Ala Phe Gly His Asp Gly Ala Ser Ala Ser Leu Gly Phe Ala Asp
                325                 330                 335 cct gtg tat gaa ctc gcc ttc ggg tac gtg ccg caa cag gcc gag ccg       1056
Pro Val Tyr Glu Leu Ala Phe Gly Tyr Val Pro Gln Gln Ala Glu Pro
            340                 345                 350 ggc gga gcg gga tgc cgc aac ctt gag ctg agc gcc gcc gtg cgg aag       1104
Gly Gly Ala Gly Cys Arg Asn Leu Glu Leu Ser Ala Ala Val Arg Lys
        355                 360                 365 gca gtc acc gaa ctg gct cag                                           1125
Ala Val Thr Glu Leu Ala Gln
    370                 375

<210> SEQ ID NO 3
<211> LENGTH: 1110
<212> TYPE: DNA
<213> ORGANISM: Chromobacterium sp.
<220> FEATURE:
<221> NAME/KEY: CDS
<222> LOCATION: (1)..(1110)

<400> SEQUENCE: 3 atg act ctg ttc gat ggt atc act tcg cga atc gta gat act gat cgt         48
Met Thr Leu Phe Asp Gly Ile Thr Ser Arg Ile Val Asp Thr Asp Arg
1               5                   10                  15 ctg act gtt aac atc ctg gaa cgt gcg gcc gac gac ccg cag acc ccg         96
Leu Thr Val Asn Ile Leu Glu Arg Ala Ala Asp Asp Pro Gln Thr Pro
                20                  25                  30 ccc gac cgc acg gtc gtg ttc gtc cac ggg aat gtg tcc tcc gcg ctg        144
Pro Asp Arg Thr Val Val Phe Val His Gly Asn Val Ser Ser Ala Leu
            35                  40                  45 ttc tgg cag gag atc atg cag gac ctg ccg agc gac ctg cgc gcc atc        192
```

-continued

```
                Phe Trp Gln Glu Ile Met Gln Asp Leu Pro Ser Asp Leu Arg Ala Ile
                    50                  55                  60 gcg gtc gac ctg cgc ggc ttc ggc ggc tcg gag cac gcg ccg gtc gac          240
Ala Val Asp Leu Arg Gly Phe Gly Gly Ser Glu His Ala Pro Val Asp
 65              70                  75                  80 gcc acc cgc ggc gtc cgc gac ttc agc gac gat ctg cac gcg acc ctc          288
Ala Thr Arg Gly Val Arg Asp Phe Ser Asp Asp Leu His Ala Thr Leu
                     85                  90                  95 gag gcg ctc gac atc ccg gtc gcg cat ctg gtc ggc tgg tcg atg ggc          336
Glu Ala Leu Asp Ile Pro Val Ala His Leu Val Gly Trp Ser Met Gly
                100                 105                 110 ggc ggc gtc gtc atg cag tat gcc ctc gac cac ccg gtg ctg agc ctg          384
Gly Gly Val Val Met Gln Tyr Ala Leu Asp His Pro Val Leu Ser Leu
            115                 120                 125 acc ctg cag tcg ccg gtg tcg ccc tac ggc ttc ggc ggc acc cgc cgt          432
Thr Leu Gln Ser Pro Val Ser Pro Tyr Gly Phe Gly Gly Thr Arg Arg
        130                 135                 140 gac ggc tca cgc ctc acc gac gac gat gcc ggc tgc ggt ggc ggc ggt          480
Asp Gly Ser Arg Leu Thr Asp Asp Asp Ala Gly Cys Gly Gly Gly Gly
145                 150                 155                 160 gcg aac ccc gac ttc atc cag cgc ctc atc gac cac gac acc tcc gac          528
Ala Asn Pro Asp Phe Ile Gln Arg Leu Ile Asp His Asp Thr Ser Asp
                165                 170                 175 gat gcg cag acc tcg ccc cgg agc gtc ttc cgc gcc ggc tac gtc gcc          576
Asp Ala Gln Thr Ser Pro Arg Ser Val Phe Arg Ala Gly Tyr Val Ala
            180                 185                 190 tcg gac tac acc acc gac cac gag gac gtg tgg gtc gaa tcg atg ctc          624
Ser Asp Tyr Thr Thr Asp His Glu Asp Val Trp Val Glu Ser Met Leu
        195                 200                 205 acc acg tcc acc gcc gac gga aac tac ccc ggc gat gcg gtg ccg agc          672
Thr Thr Ser Thr Ala Asp Gly Asn Tyr Pro Gly Asp Ala Val Pro Ser
    210                 215                 220 gac aac tgg ccg ggc ttc gcc gcc ggc cgc cac ggc gtg ctg aac acc          720
Asp Asn Trp Pro Gly Phe Ala Ala Gly Arg His Gly Val Leu Asn Thr
225                 230                 235                 240 atg gcc ccg cag tac ttc gat gtg tcg ggg att gtc gac ctg gcc gag          768
Met Ala Pro Gln Tyr Phe Asp Val Ser Gly Ile Val Asp Leu Ala Glu
                245                 250                 255 aag cct ccg atc ctg tgg atc cac ggc acc gcg gac gcg atc gtc tcc          816
Lys Pro Pro Ile Leu Trp Ile His Gly Thr Ala Asp Ala Ile Val Ser
            260                 265                 270 gac gcg tcg ttc tac gac ctc aac tac ctc ggc cag ctg ggc atc gtc          864
Asp Ala Ser Phe Tyr Asp Leu Asn Tyr Leu Gly Gln Leu Gly Ile Val
        275                 280                 285 ccc ggc tgg ccc ggc gaa gac gtc gcg ccc gcg cag gag atg gtg tcg          912
Pro Gly Trp Pro Gly Glu Asp Val Ala Pro Ala Gln Glu Met Val Ser
    290                 295                 300 cag acc cgc gat gtc ctc ggc cgc tac gct gcg ggc ggc gga acg gtc          960
Gln Thr Arg Asp Val Leu Gly Arg Tyr Ala Ala Gly Gly Gly Thr Val
305                 310                 315                 320 acc gag gtc gcc gtc gag ggc gcg ggc cac tcc gcg cac ctg gag cgt         1008
Thr Glu Val Ala Val Glu Gly Ala Gly His Ser Ala His Leu Glu Arg
                325                 330                 335 ccc gcg gtg ttc cgc cac gcg ctg ctc gag atc atc ggc tac gtc ggc         1056
Pro Ala Val Phe Arg His Ala Leu Leu Glu Ile Ile Gly Tyr Val Gly
            340                 345                 350 gcg gcg gcc gac ccc gcc ccg ccg acc gag gcg atc atc atc cgc tcc         1104
Ala Ala Ala Asp Pro Ala Pro Pro Thr Glu Ala Ile Ile Ile Arg Ser
        355                 360                 365
```

```
      gcc gac                                                       1110
      Ala Asp
          370

<210> SEQ ID NO 4
<211> LENGTH: 33
<212> TYPE: PRT
<213> ORGANISM: Escherichia coli

<400> SEQUENCE: 4

Met Lys Gln Ser Thr Ile Ala Leu Ala Leu Leu Pro Leu Leu Phe Thr
 1               5                  10                  15

Pro Val Ala Asn Ala Ala Pro Thr Ser Asn Pro Ala Gln Glu Leu Glu
            20                  25                  30

Ala

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aacgaattcc tsagygt                                                   17

<210> SEQ ID NO 6
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
catgaaacaa agcactattg cactggcact cttaccgtta ctgtttaccc ctgtggcaaa    60
cg                                                                   62

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cagcgccgac cagcaacccg gcacaggaac tgg                                 33

<210> SEQ ID NO 8
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
aaacagtaac ggtaagagtg ccagtgcaat agtgctttgt tt                       42

<210> SEQ ID NO 9
<211> LENGTH: 53
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 9
aattccagtt cctgtgccgg gttgctggtc ggcgctgcgt ttgccacagg ggt        53

<210> SEQ ID NO 10
<211> LENGTH: 255
<212> TYPE: PRT
<213> ORGANISM: Aspergillus flavus

<400> SEQUENCE: 10
```

| | | | | | | | | | | | | | | | |
|---|---|---|---|---|---|---|---|---|---|---|---|---|---|---|---|
| Met | His | Leu | Pro | Ile | Lys | Thr | Leu | Phe | Val | Ser | Leu | Leu | Gly | Ala | Ser |
| 1 | | | | 5 | | | | | 10 | | | | | 15 | |
| Val | Leu | Ala | Arg | Pro | Leu | Pro | Asn | Asp | Ala | Leu | Val | Glu | Arg | Asn | Ala |
| | | | 20 | | | | | 25 | | | | | 30 | | |
| Pro | Leu | Asn | Glu | Phe | Leu | Ser | Val | Leu | Leu | Ser | His | Leu | Pro | Ala | Ile |
| | | | 35 | | | | | 40 | | | | | 45 | | |
| Asn | Gly | Ser | Ile | Thr | Ala | Val | Ser | Gly | Leu | Ile | Thr | Asp | Phe | Asp | Gln |
| | 50 | | | | | 55 | | | | | 60 | | | | |
| Leu | Leu | Ala | Asp | Ile | Thr | Gly | Ala | Gln | Thr | Thr | Leu | Asn | Gly | Phe | Thr |
| 65 | | | | | 70 | | | | | 75 | | | | | 80 |
| Gly | Ala | Cys | Thr | Asp | Tyr | Thr | Val | Leu | Phe | Ala | Arg | Gly | Thr | Ser | Glu |
| | | | | 85 | | | | | 90 | | | | | 95 | |
| Pro | Gly | Asn | Val | Gly | Val | Leu | Val | Gly | Pro | Pro | Leu | Ala | Glu | Ala | Phe |
| | | | 100 | | | | | 105 | | | | | 110 | | |
| Glu | Gly | Ala | Val | Gly | Ala | Ser | Ala | Leu | Ser | Phe | Gln | Gly | Val | Asn | Gly |
| | | | 115 | | | | | 120 | | | | | 125 | | |
| Tyr | Ser | Ala | Ser | Val | Glu | Gly | Tyr | Leu | Ala | Gly | Glu | Ala | Ala | Gly |
| | 130 | | | | | 135 | | | | | 140 | | | | |
| Ser | Lys | Ala | Met | Ala | Ser | Gln | Ala | Ser | Asp | Ile | Leu | Ser | Lys | Cys | Pro |
| 145 | | | | | 150 | | | | | 155 | | | | | 160 |
| Asp | Thr | Lys | Leu | Val | Met | Ser | Gly | Tyr | Ser | Gln | Gly | Cys | Gln | Ile | Val |
| | | | | 165 | | | | | 170 | | | | | 175 | |
| His | Asn | Ala | Val | Glu | Gln | Leu | Pro | Ala | Glu | His | Ala | Ser | Lys | Ile | Ser |
| | | | 180 | | | | | 185 | | | | | 190 | | |
| Ser | Val | Leu | Leu | Phe | Gly | Asp | Pro | Tyr | Lys | Gly | Lys | Ala | Leu | Pro | Asn |
| | | | 195 | | | | | 200 | | | | | 205 | | |
| Val | Asp | Ala | Ser | Arg | Val | His | Thr | Val | Cys | His | Ala | Gly | Asp | Thr | Ile |
| | 210 | | | | | 215 | | | | | 220 | | | | |
| Cys | Glu | Asn | Ser | Val | Ile | Ile | Leu | Pro | Ala | His | Leu | Thr | Tyr | Ala | Val |
| 225 | | | | | 230 | | | | | 235 | | | | | 240 |
| Asp | Val | Ala | Ser | Ala | Ala | Asp | Phe | Ala | Val | Ala | Ala | Lys | Asn | | |
| | | | | 245 | | | | | 250 | | | | | 255 | |

```
<210> SEQ ID NO 11
<211> LENGTH: 375
<212> TYPE: PRT
<213> ORGANISM: Arthrobacter globiformis

<400> SEQUENCE: 11
```

| | | | | | | | | | | | | | | | |
|---|---|---|---|---|---|---|---|---|---|---|---|---|---|---|---|
| Val | Asp | Ala | Gln | Thr | Ile | Ala | Pro | Gly | Phe | Glu | Ser | Val | Ala | Glu | Leu |
| 1 | | | | 5 | | | | | 10 | | | | | 15 | |
| Phe | Gly | Arg | Phe | Leu | Ser | Glu | Asp | Arg | Glu | Tyr | Ser | Ala | Gln | Leu | Ala |
| | | | 20 | | | | | 25 | | | | | 30 | | |
| Ala | Tyr | His | Arg | Gly | Val | Lys | Val | Leu | Asp | Ile | Ser | Gly | Gly | Pro | His |

```
                35                  40                  45
Arg Arg Pro Asp Ser Val Thr Gly Val Phe Ser Cys Ser Lys Gly Val
 50                  55                  60

Ser Gly Leu Val Ile Ala Leu Val Gln Asp Gly Phe Leu Asp Leu
 65                  70                  75                  80

Asp Ala Glu Val Val Lys Tyr Trp Pro Glu Phe Gly Ala Glu Gly Lys
                 85                  90                  95

Ala Thr Ile Thr Val Ala Gln Leu Leu Ser His Gln Ala Gly Leu Leu
                100                 105                 110

Gly Val Glu Gly Gly Leu Thr Leu Ala Glu Tyr Asn Asn Ser Glu Leu
                115                 120                 125

Ala Ala Ala Lys Leu Ala Gln Met Arg Pro Leu Trp Lys Pro Gly Thr
130                 135                 140

Ala Phe Gly Tyr His Ala Leu Thr Ile Gly Val Phe Met Glu Glu Leu
145                 150                 155                 160

Cys Arg Arg Ile Thr Gly Ser Thr Leu Gln Glu Ile Tyr Glu Gln Arg
                165                 170                 175

Ile Arg Ser Val Thr Gly Ala His Phe Phe Leu Gly Leu Pro Glu Ser
                180                 185                 190

Glu Glu Pro Arg Tyr Ala Thr Leu Arg Trp Ala Ala Asp Pro Ser Gln
                195                 200                 205

Pro Trp Ile Asp Pro Ala Ser His Phe Gly Leu Ser Ala Asn Ser Ala
                210                 215                 220

Val Gly Asp Ile Leu Asp Leu Pro Asn Leu Arg Glu Val Arg Ala Ala
225                 230                 235                 240

Gly Leu Ser Ser Ala Ala Gly Val Ala Ser Ala Glu Gly Met Ala Arg
                245                 250                 255

Val Tyr Ala Ala Ala Leu Thr Gly Leu Ala Ala Asn Gly Asp Arg Ala
                260                 265                 270

Ala Val Ala Pro Leu Leu Ser Glu Glu Thr Ile Gln Thr Val Thr Ala
                275                 280                 285

Glu Gln Val Phe Gly Ile Asp Arg Val Phe Gly Glu Thr Ser Cys Phe
290                 295                 300

Gly Thr Val Phe Met Lys Ser His Ala Arg Ser Pro Tyr Gly Ser Tyr
305                 310                 315                 320

Arg Ala Phe Gly His Asp Gly Ala Ser Ala Ser Leu Gly Phe Ala Asp
                325                 330                 335

Pro Val Tyr Glu Leu Ala Phe Gly Tyr Val Pro Gln Gln Ala Glu Pro
                340                 345                 350

Gly Gly Ala Gly Cys Arg Asn Leu Glu Leu Ser Ala Ala Val Arg Lys
                355                 360                 365

Ala Val Thr Glu Leu Ala Gln
        370                 375

<210> SEQ ID NO 12
<211> LENGTH: 370
<212> TYPE: PRT
<213> ORGANISM: Chromobacterium sp.

<400> SEQUENCE: 12

Met Thr Leu Phe Asp Gly Ile Thr Ser Arg Ile Val Asp Thr Asp Arg
 1               5                  10                  15

Leu Thr Val Asn Ile Leu Glu Arg Ala Ala Asp Asp Pro Gln Thr Pro
                20                  25                  30
```

-continued

```
Pro Asp Arg Thr Val Val Phe Val His Gly Asn Val Ser Ser Ala Leu
    35                  40                  45
Phe Trp Gln Glu Ile Met Gln Asp Leu Pro Ser Asp Leu Arg Ala Ile
 50                  55                  60
Ala Val Asp Leu Arg Gly Phe Gly Ser Glu His Ala Pro Val Asp
 65                  70                  75                  80
Ala Thr Arg Gly Val Arg Asp Phe Ser Asp Asp Leu His Ala Thr Leu
                 85                  90                  95
Glu Ala Leu Asp Ile Pro Val Ala His Leu Val Gly Trp Ser Met Gly
                100                 105                 110
Gly Gly Val Met Gln Tyr Ala Leu Asp His Pro Val Leu Ser Leu
             115                 120                 125
Thr Leu Gln Ser Pro Val Ser Pro Tyr Gly Phe Gly Thr Arg Arg
130                 135                 140
Asp Gly Ser Arg Leu Thr Asp Asp Ala Gly Cys Gly Gly Gly
145                 150                 155                 160
Ala Asn Pro Asp Phe Ile Gln Arg Leu Ile Asp His Asp Thr Ser Asp
                165                 170                 175
Asp Ala Gln Thr Ser Pro Arg Ser Val Phe Arg Ala Gly Tyr Val Ala
            180                 185                 190
Ser Asp Tyr Thr Thr Asp His Glu Asp Val Trp Val Glu Ser Met Leu
            195                 200                 205
Thr Thr Ser Thr Ala Asp Gly Asn Tyr Pro Gly Asp Ala Val Pro Ser
210                 215                 220
Asp Asn Trp Pro Gly Phe Ala Ala Gly Arg His Gly Val Leu Asn Thr
225                 230                 235                 240
Met Ala Pro Gln Tyr Phe Asp Val Ser Gly Ile Val Asp Leu Ala Glu
                245                 250                 255
Lys Pro Pro Ile Leu Trp Ile His Gly Thr Ala Asp Ala Ile Val Ser
                260                 265                 270
Asp Ala Ser Phe Tyr Asp Leu Asn Tyr Leu Gly Gln Leu Gly Ile Val
            275                 280                 285
Pro Gly Trp Pro Gly Glu Asp Val Ala Pro Ala Gln Glu Met Val Ser
290                 295                 300
Gln Thr Arg Asp Val Leu Gly Arg Tyr Ala Ala Gly Gly Thr Val
305                 310                 315                 320
Thr Glu Val Ala Val Glu Gly Ala Gly His Ser Ala His Leu Glu Arg
                325                 330                 335
Pro Ala Val Phe Arg His Ala Leu Leu Glu Ile Ile Gly Tyr Val Gly
            340                 345                 350
Ala Ala Ala Asp Pro Ala Pro Pro Thr Glu Ala Ile Ile Ile Arg Ser
            355                 360                 365
Ala Asp
370
```

<210> SEQ ID NO 13
<211> LENGTH: 370
<212> TYPE: PRT
<213> ORGANISM: Chromobacterium sp.
<220> FEATURE:
<221> NAME/KEY: MOD_RES
<222> LOCATION: (160)
<223> OTHER INFORMATION: Ala, Val, Leu, or Ser
<220> FEATURE:
<221> NAME/KEY: MOD_RES
<222> LOCATION: (189)
<223> OTHER INFORMATION: Ala, Val, Leu, Iso, Ser, Thr, Phe, His, Tyr, or Arg

<400> SEQUENCE: 13

```
Met Thr Leu Phe Asp Gly Ile Thr Ser Arg Ile Val Asp Thr Asp Arg
  1               5                  10                  15

Leu Thr Val Asn Ile Leu Glu Arg Ala Ala Asp Pro Gln Thr Pro
             20                  25                  30

Pro Asp Arg Thr Val Val Phe Val His Gly Asn Val Ser Ser Ala Leu
         35                  40                  45

Phe Trp Gln Glu Ile Met Gln Asp Leu Pro Ser Asp Leu Arg Ala Ile
     50                  55                  60

Ala Val Asp Leu Arg Gly Phe Gly Gly Ser Glu His Ala Pro Val Asp
 65                  70                  75                  80

Ala Thr Arg Gly Val Arg Asp Phe Ser Asp Leu His Ala Thr Leu
             85                  90                  95

Glu Ala Leu Asp Ile Pro Val Ala His Leu Val Gly Trp Ser Met Gly
             100                 105                 110

Gly Gly Val Val Met Gln Tyr Ala Leu Asp His Pro Val Leu Ser Leu
         115                 120                 125

Thr Leu Gln Ser Pro Val Ser Pro Tyr Gly Phe Gly Gly Thr Arg Arg
 130                 135                 140

Asp Gly Ser Arg Leu Thr Asp Asp Ala Gly Cys Gly Gly Gly Xaa
145                 150                 155                 160

Ala Asn Pro Asp Phe Ile Gln Arg Leu Ile Asp His Asp Thr Ser Asp
             165                 170                 175

Asp Ala Gln Thr Ser Pro Arg Ser Val Phe Arg Ala Xaa Tyr Val Ala
             180                 185                 190

Ser Asp Tyr Thr Thr Asp His Glu Asp Val Trp Val Glu Ser Met Leu
         195                 200                 205

Thr Thr Ser Thr Ala Asp Gly Asn Tyr Pro Gly Asp Ala Val Pro Ser
 210                 215                 220

Asp Asn Trp Pro Gly Phe Ala Ala Gly Arg His Gly Val Leu Asn Thr
225                 230                 235                 240

Met Ala Pro Gln Tyr Phe Asp Val Ser Gly Ile Val Asp Leu Ala Glu
             245                 250                 255

Lys Pro Pro Ile Leu Trp Ile His Gly Thr Ala Asp Ala Ile Val Ser
             260                 265                 270

Asp Ala Ser Phe Tyr Asp Leu Asn Tyr Leu Gly Gln Leu Gly Ile Val
         275                 280                 285

Pro Gly Trp Pro Gly Glu Asp Val Ala Pro Ala Gln Glu Met Val Ser
 290                 295                 300

Gln Thr Arg Asp Val Leu Gly Arg Tyr Ala Ala Gly Gly Gly Thr Val
305                 310                 315                 320

Thr Glu Val Ala Val Glu Gly Ala Gly His Ser Ala His Leu Glu Arg
             325                 330                 335

Pro Ala Val Phe Arg His Ala Leu Leu Glu Ile Ile Gly Tyr Val Gly
             340                 345                 350

Ala Ala Ala Asp Pro Ala Pro Pro Thr Glu Ala Ile Ile Ile Arg Ser
         355                 360                 365

Ala Asp
 370
```